(12) United States Patent
Farley et al.

(10) Patent No.: US 8,360,971 B2
(45) Date of Patent: *Jan. 29, 2013

(54) SURGICAL RETRACTOR ANGLING DEVICE

(75) Inventors: Daniel K. Farley, Traverse City, MI (US); Steven Nowak, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 58 days.

This patent is subject to a terminal disclaimer.

(21) Appl. No.: 12/817,955

(22) Filed: Jun. 17, 2010

(65) Prior Publication Data

US 2010/0256454 A1 Oct. 7, 2010

Related U.S. Application Data

(63) Continuation-in-part of application No. 12/391,917, filed on Feb. 24, 2009.

(51) Int. Cl.
  *A61B 1/32* (2006.01)
(52) U.S. Cl. ......................... 600/213; 600/215
(58) Field of Classification Search ........... 600/201–249
  See application file for complete search history.

(56) References Cited

U.S. PATENT DOCUMENTS

| | | | |
|---|---|---|---|
| 4,971,038 A | 11/1990 | Farley | |
| 5,902,233 A | 5/1999 | Farley et al. | |
| 5,984,865 A | 11/1999 | Farley et al. | |
| 6,206,826 B1 | 3/2001 | Mathews | |
| 2005/0215865 A1* | 9/2005 | LeVahn et al. | 600/231 |

OTHER PUBLICATIONS

Patent Cooperation Treaty, Notification of Transmittal of the International Search Report and the Written Opinion of the International Searching Authority, in International Application No. PCT/US2011/04662, dated Oct. 11, 2011.

* cited by examiner

*Primary Examiner* — Alvin Stewart
*Assistant Examiner* — Nicholas Plionis
(74) *Attorney, Agent, or Firm* — McAndrews, Held & Malloy, Ltd.

(57) ABSTRACT

Surgical retractor systems including removable angling devices and methods of use are provided. A surgical retractor system can include a head with an opening, a blade including a nipple, and an angling device including a handle. The nipple can include a first recess that runs circumferentially around an exterior surface of the nipple and terminates at a flange. The opening can be configured to receive the nipple. The nipple can be longer than the opening such that the flange and at least a portion of the recess extend beyond an end of the opening when the blade is attached to the head. The angling device can be configured to receive the flange such that the angling device can be removably attached to the flange. The angling device can be used to manipulate the position of the blade when the angling device is attached to the flange.

11 Claims, 12 Drawing Sheets

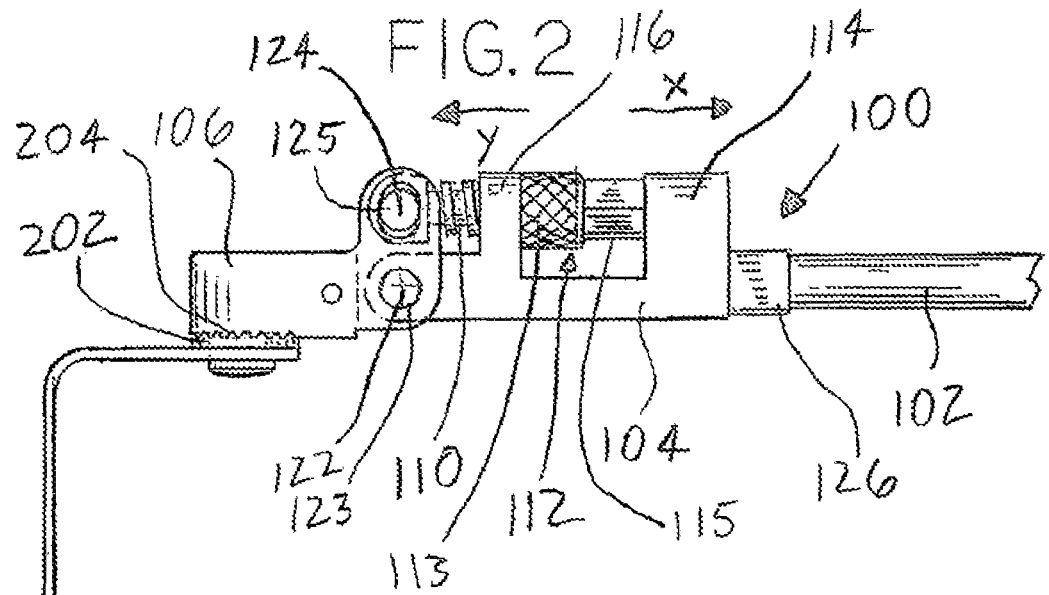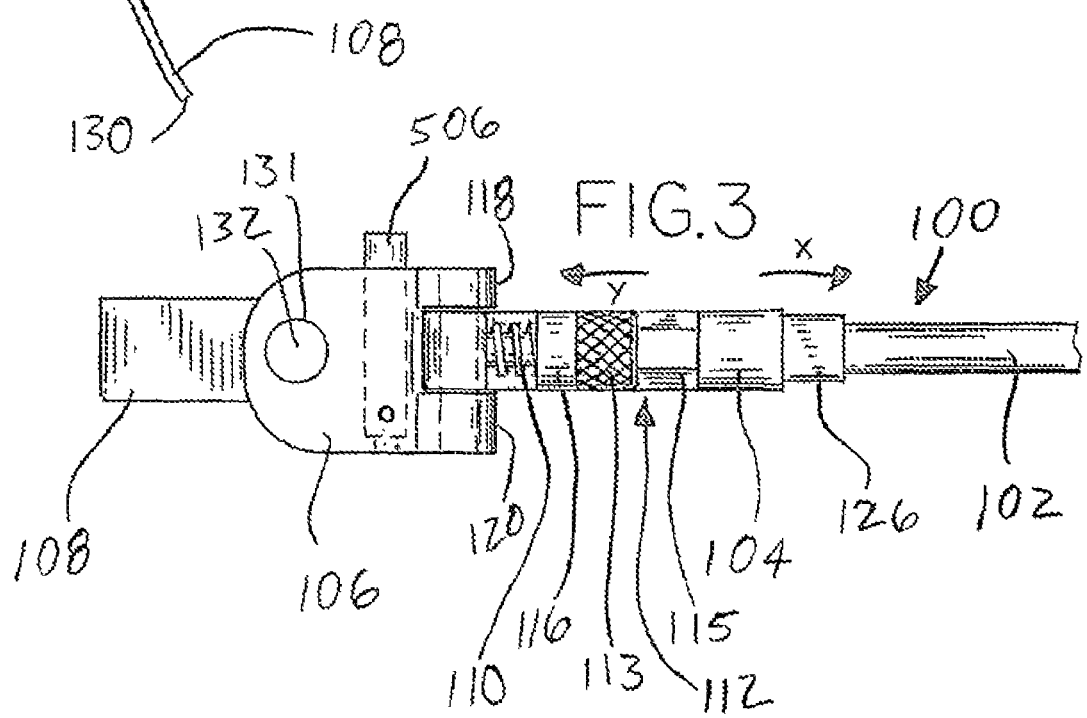

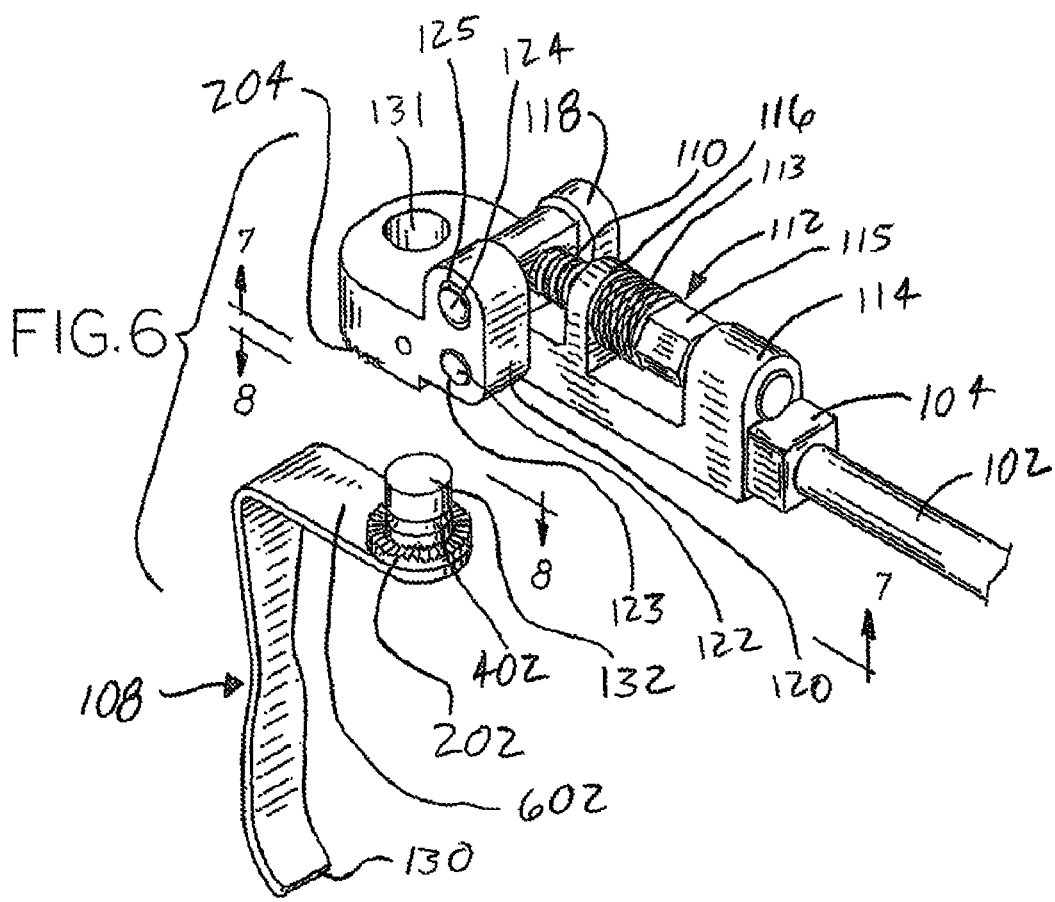
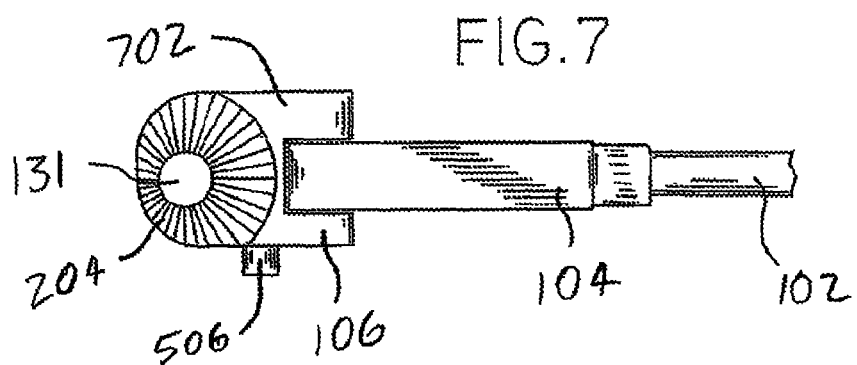
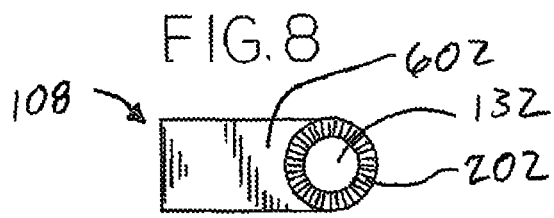

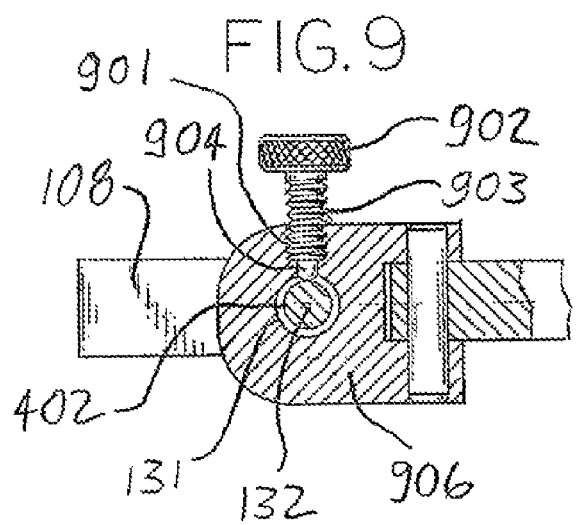
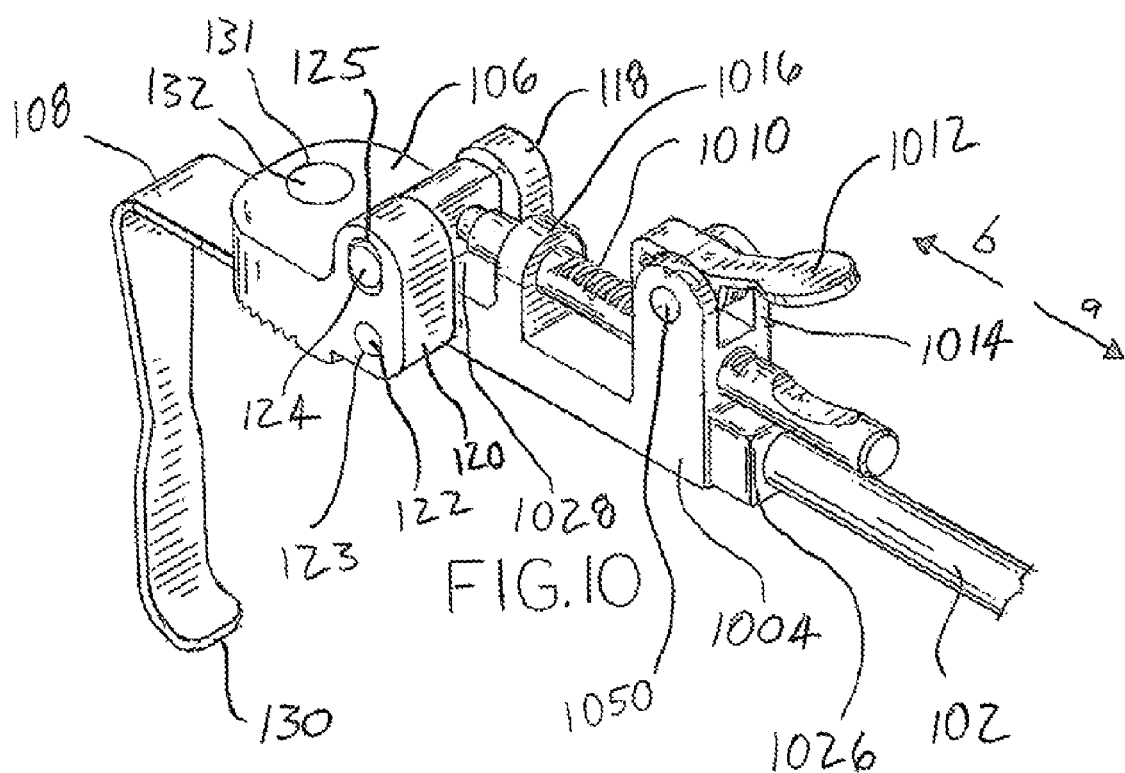

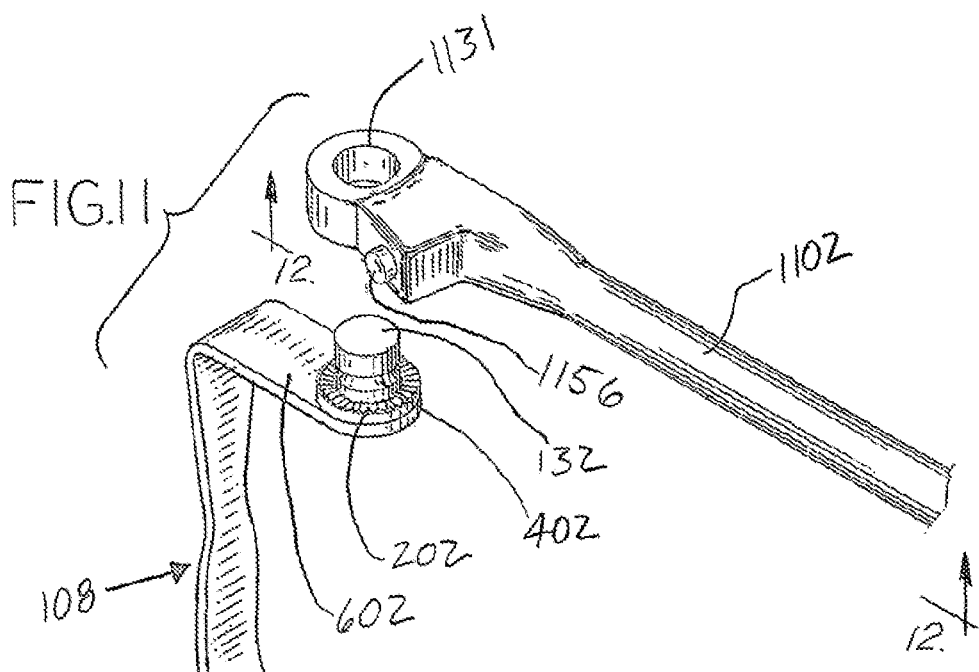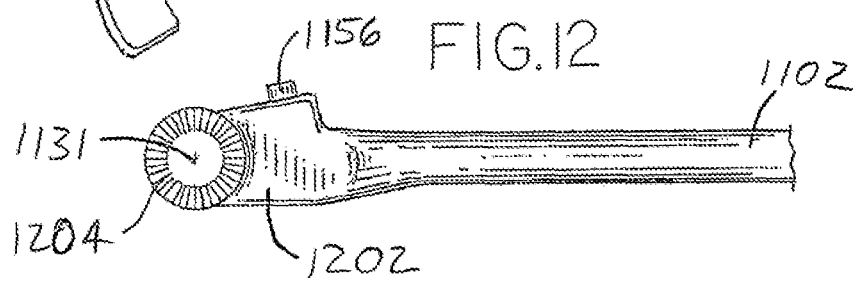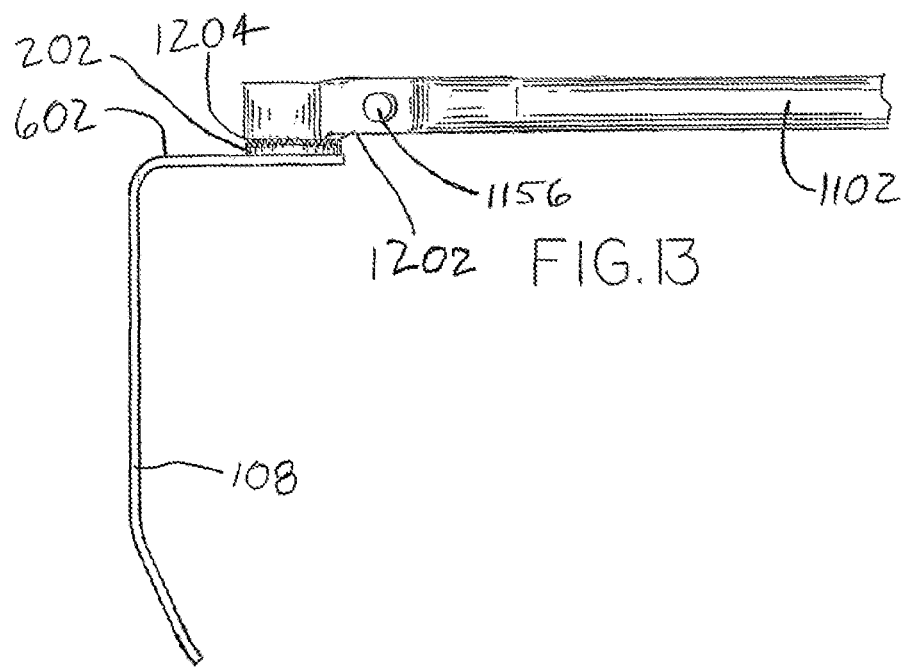

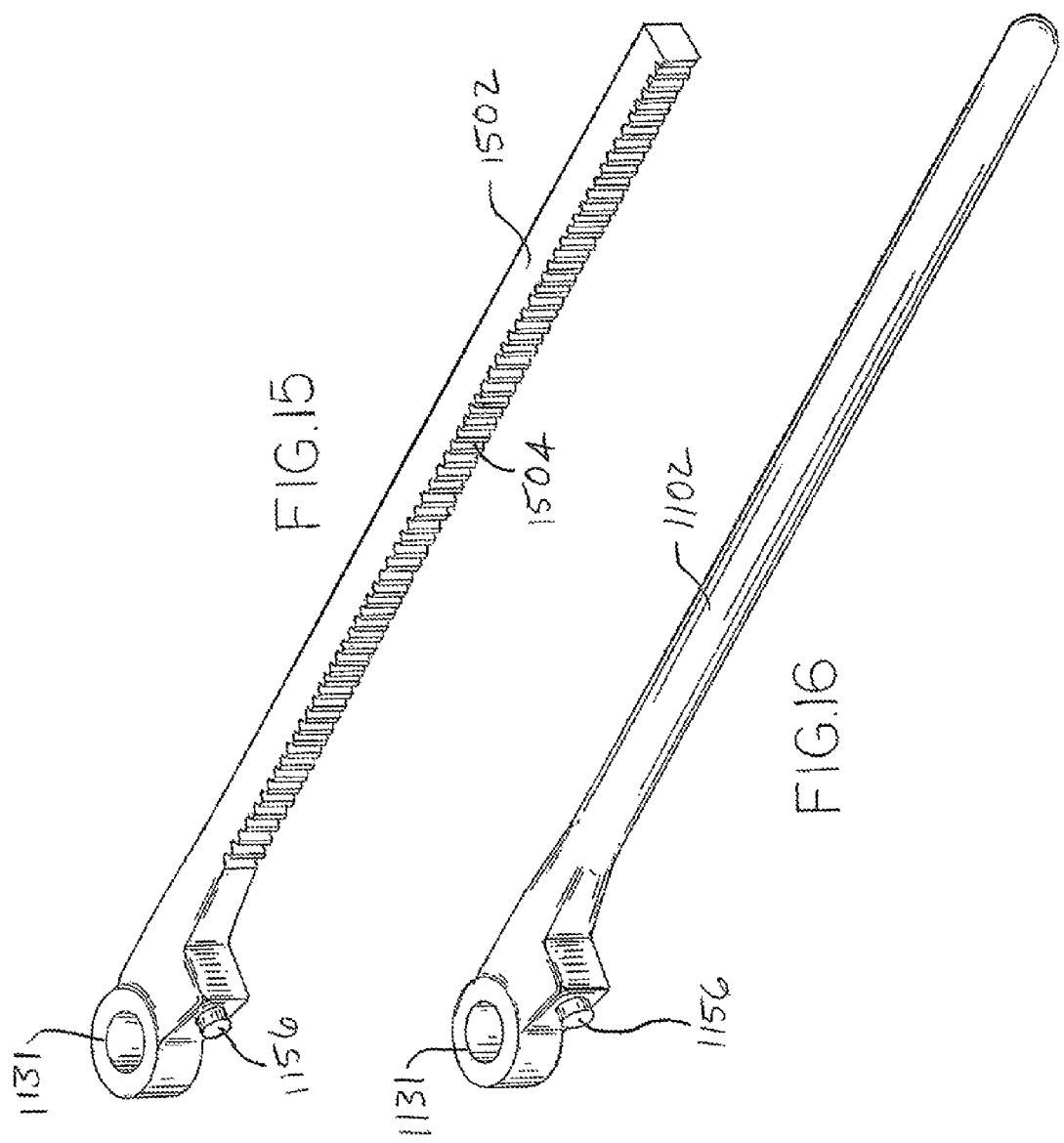

SURGICAL RETRACTOR ANGLING DEVICE

RELATED APPLICATIONS

This application is a continuation-in-part of U.S. patent application Ser. No. 12/391,917 filed Feb. 24, 2009, and entitled "Surgical Retractor with Locking Blade," which application is incorporated by reference herein in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present technology relates to surgical devices for retracting anatomy to provide exposure to an operating site and to properly retain tissue surrounding a surgical incision. In surgical operations, it is particularly important that a patient's abdominal region be well exposed to facilitate work by a surgeon. To effect this desired exposure, surgical retractors are normally employed which engage and hold the skin apart at the incision during the course of the operation.

Most retractors comprise an arm connected to a blade. The blade can be of a variety of constructions including, for example, a paddle-like design or a finger-like configuration. The type of retractor blade used depends on a number of factors including, the size of the incision, the size of the patient and the type of surgery to be performed.

Oftentimes, a surgeon is required to change the type of retractor blade being used, during the course of an operation. To this end, a variety of interchangeable retractor blade systems have been proposed which allow for the blade to be quickly released from the retractor handle whereby one blade can be removed and another put in its place. This type of arrangement allows a single retractor arm to be used with a variety of blades. In addition, certain quick release retractor blades can swivel in place to compensate for inexact positioning of an arm.

Some known surgical retractors are described, for example, in U.S. Pat. No. 5,984,865 entitled "SURGICAL RETRACTOR HAVING LOCKING INTERCHANGEABLE BLADES", which issued Nov. 16, 1999 to Farley et al., U.S. Pat. No. 5,902,233 entitled "ANGLING SURGICAL RETRACTOR APPARATUS AND METHOD OF RETRACTING ANATOMY", which issued May 11, 1999 to Farley et al. and U.S. Pat. No. 4,971,038 entitled "TABLE MOUNTED SURGICAL RETRACTOR", which issued Nov. 29, 1990 to Farley, each of which are incorporated herein by reference in their entirety.

It is desirable to provide improved surgical retractors with improved functionality, such as those described herein.

BRIEF SUMMARY OF THE INVENTION

Embodiments of the present technology provide, for example, a surgical retractor system including a removable angling device and methods of using such a surgical retractor system.

For example, in an embodiment, a surgical retractor system includes: a head with an opening; a blade comprising a nipple including a first recess that runs circumferentially around an exterior surface of the nipple and terminates at a flange, wherein the opening is configured to receive the nipple, and wherein the nipple is longer than the opening such that the flange and at least a portion of the recess extend beyond an end of the opening when the blade is attached to the head; and an angling device comprising a handle, the angling device configured to receive the flange such that the angling device can be removably attached to the flange, wherein the angling device can be used to manipulate the position of the blade when the angling device is attached to the flange.

For example, in an embodiment, the angling device can be used to rotate the blade radially about the opening when the angling device is attached to the flange.

For example, in an embodiment, a surgical retractor system further includes an arm and a connector configured to attach the arm to the head, the connector configured to provide for angular displacement of the head relative to the arm.

For example, in an embodiment, the angling device can be used to angularly displace the head relative to the arm.

For example, in an embodiment, the connector comprises a notched shaft and a spring loaded lever, manipulating the spring loaded lever can release the notched shaft such that the shaft can be translated, and translation of the shaft can provide angular displacement of the head relative to the arm.

For example, in an embodiment, the notched shaft and the spring loaded lever are configured to work as a ratchet, such that when the shaft and the lever are engaged, translation of the shaft in a first direction is restricted and translation of the shaft in a second direction opposite the first direction is not restricted.

For example, in an embodiment, the flange is circular.

For example, in an embodiment, the angling device is configured to extend from the head at an angle.

For example, in an embodiment, the angling device includes a slot configured to receive the flange.

For example, in an embodiment, the slot is configured to have a varied clearance that decreases deeper into the slot, such that sliding the flange deeper into the slot can increase tension between the flange and the slot.

For example, in an embodiment, a method of using a surgical retractor system includes: attaching a blade to a head by inserting a nipple on the blade into an opening on the head, wherein the nipple includes a first recess that runs circumferentially around an exterior surface of the nipple and terminates at a flange, and wherein the nipple is longer than the opening such that the flange and at least a portion of the recess extend beyond an end of the opening when the blade is attached to the head; and removably attaching an angling device to the flange, the angling device comprising a handle, wherein the angling device can be used to manipulate the position of the blade.

For example, in an embodiment, a method of using a surgical retractor system further includes using the angling device to rotate the blade radially about the opening.

For example, in an embodiment, the head is attached to a connector and the connector is attached to an arm, and the connector is configured to provide for angular displacement of the head relative to the arm.

For example, in an embodiment, a method of using a surgical retractor system further includes using the angling device to angularly displace the head relative to the arm.

For example, in an embodiment, the connector comprises a notched shaft and a spring loaded lever, manipulating the spring loaded lever can release the notched shaft such that the shaft can be translated, and translation of the shaft provides angular displacement of the head relative to the arm.

For example, in an embodiment, the notched shaft and the spring loaded lever are configured to work as a ratchet, such that when the shaft and the lever are engaged, translation of the shaft in a first direction is restricted and translation of the shaft in a second direction opposite the first direction is not restricted.

For example, in an embodiment, the flange is circular.

For example, in an embodiment, the angling device is configured to extend from the head at an angle.

For example, in an embodiment, the angling device includes a slot configured to receive the flange.

For example, in an embodiment, the slot is configured to have a varied clearance that decreases deeper into the slot, such that sliding the flange deeper into the slot increases tension between the flange and the slot.

BRIEF DESCRIPTION OF SEVERAL VIEWS OF THE DRAWINGS

FIG. 2 depicts a side view of a portion of the surgical retractor depicted in FIG. 1.

FIG. 3 depicts a top view of a portion of the surgical retractor depicted in FIG. 1.

FIG. 6 depicts an exploded perspective view of a portion of the surgical retractor depicted in FIG. 1.

FIG. 7 depicts a bottom view of a portion of the surgical retractor depicted in FIG. 6 about line 7-7.

FIG. 8 depicts a top view of a portion of the surgical retractor depicted in FIG. 6 about line 8-8.

FIG. 9 depicts a top-sectional view of a portion of a surgical retractor used in accordance with an embodiment of the present technology.

FIG. 10 depicts a perspective view of a surgical retractor used in accordance with an embodiment of the present technology.

FIG. 11 depicts an exploded perspective view of a portion of a surgical retractor used in accordance with an embodiment of the present technology.

FIG. 12 depicts a bottom view of a portion of the surgical retractor depicted in FIG. 11 about line 12-12.

FIG. 13 depicts an assembled side view of the portion of the surgical retractor depicted in FIG. 11.

FIG. 15 depicts a perspective view of a portion of a surgical retractor used in accordance with an embodiment of the present technology.

FIG. 16 depicts a perspective view of a portion of the surgical retractor depicted in FIG. 11.

Figure 1:
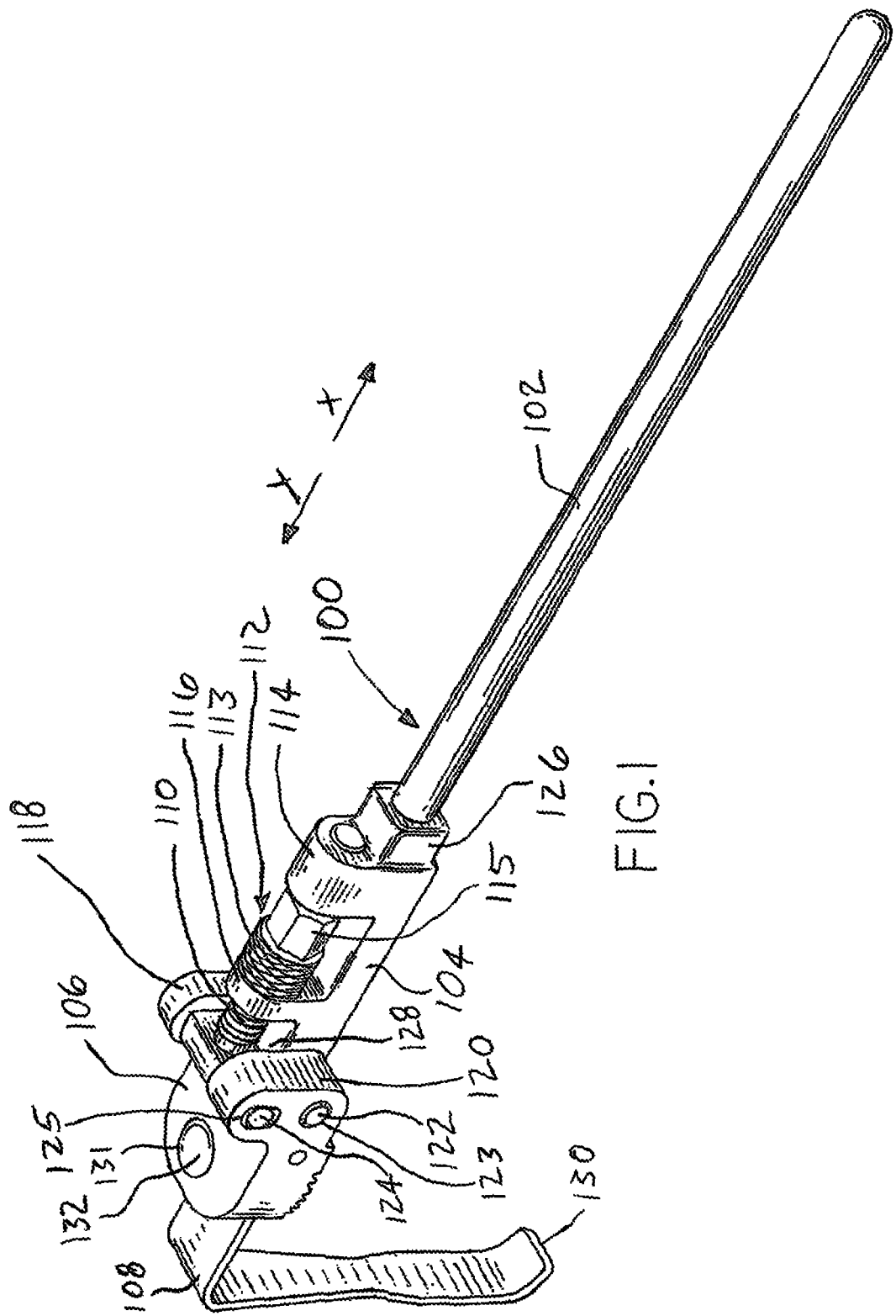
FIG. 1 depicts a perspective view of a surgical retractor used in accordance with an embodiment of the present technology.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

In the application, like elements are identified with like numerals.

FIGS. 1-6 depict a surgical retractor 100 used in accordance with an embodiment of the present technology. The surgical retractor 100 includes an arm 102, a connector 104, a head 106 and a blade 108. The arm 102 is configured to be attachable to a stationary device, such as a medical table, for example. The connector 104 is configured to movably attach the head 106 to the arm 102. That is, the head 106 is attached to the connector 104 such that the head 106 can be angularly displaced relative to the arm 102. The blade 108 is configured to be movably and removably attached to the head 106. The blade 108 is configured such that it can be released from the head, thereby allowing the blade 108 to be removed completely from the head 106 or to swivel relative to the head 106. The blade 108 is also configured such that it can be secured to the head 106 in any of a plurality of positions.

The connector 104 includes a first end 126 that is attachable to the arm 102. For example, in certain embodiments, the first end 126 can be soldered to the arm 102. The connector also includes a second end 128 (opposite the first end 126) that is attachable to the head 106. The second end 128 includes an opening configured to receive a pin 122. The head 106 includes a neck portion comprising opposing side walls, 118, 120. Each side wall 118, 120 of the head 106 is configured to receive the pin 122 in a circular opening 123. The connector 104 also includes an externally threaded shaft 110 and an internally threaded nut 112. One end of the shaft 110 includes an opening configured to receive a pin 124. Each side wall 118, 120 of the head 106 is configured to receive the pin 124 in an opening 125. In operation, translation of the shaft 110 can exert a force on pin 124, thereby causing rotation of the head 106 about pin 122. The side wall openings 125 in the head 106 are round on the ends and flat on the sides and allow the pin 124 to translate about the opening 125 during rotation of the head 106 about pin 122.

Figure 4:
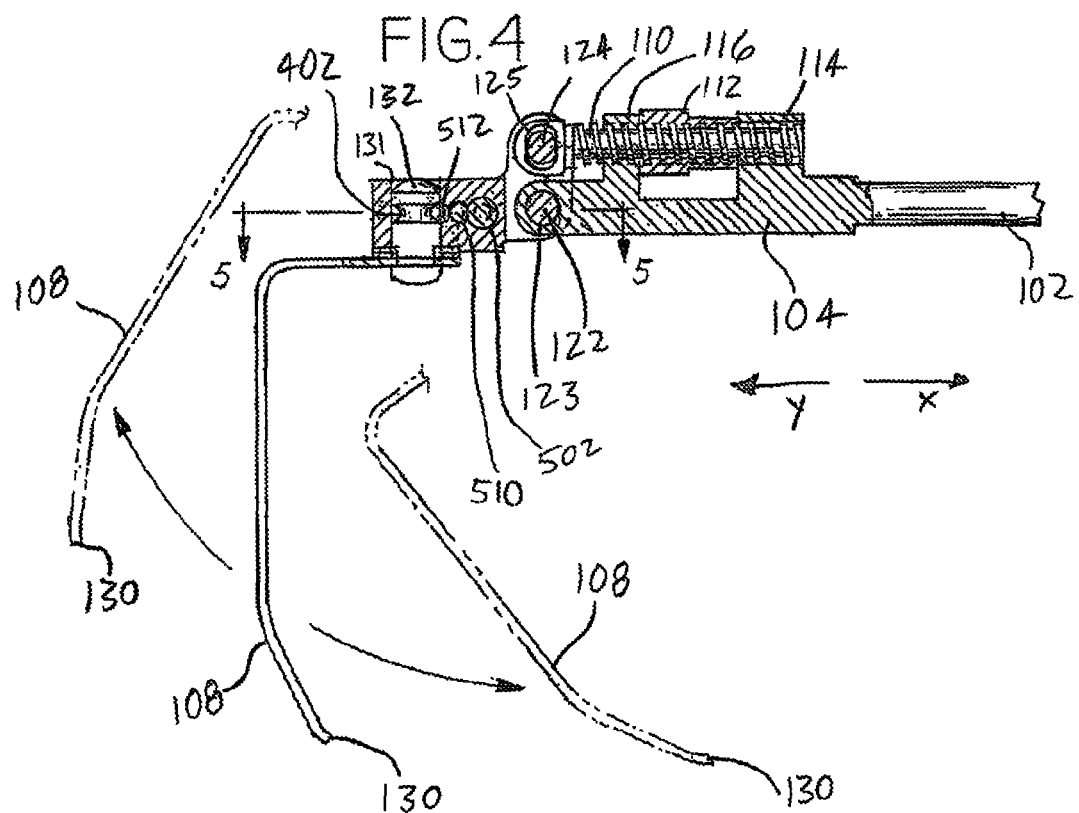
FIG. 4 depicts a side-sectional view of a portion of the surgical retractor depicted in FIG. 1.

The internally threaded nut 112 is configured to receive the externally threaded shaft 110. The nut 112 includes an exterior surface with a first portion 113 that is generally cylindrical and textured to aid a user in gripping the surface. The exterior surface of the nut 112 also includes a second portion 115 that is generally hexagonal such that a user can grip the surface, for example, with a mechanical device such as a wrench. The nut 112 is held captive between a first wall 114 and a second wall 116, each wall including an opening configured to receive the shaft 110. Manipulating the nut 112 in a first direction about the shaft 110 causes the shaft 110 to translate in a direction x. Translation of the shaft 110 in the direction x exerts a force on pin 124, thereby causing rotation of the head 106 about pin 122. As best shown in FIG. 4, this results in angular displacement of the blade 108 such that the distal end 130 of the blade 108 moves away from the arm 102. Manipulating the nut 112 about the shaft 110 in a direction opposite the first direction causes the shaft 110 to translate in a direction y that is opposite the direction x. Translation of the shaft 110 in the direction y exerts a force on pin 124, thereby causing rotation of the head 106 about pin 122. As best shown in FIG. 4, this results in angular displacement of the blade 108 such that the distal end 130 of the blade 108 moves toward the arm 102.

The blade 108 includes a nipple 132 extending therefrom that is configured to be received by the head 106. The nipple 132 is generally cylindrical and includes a recess 402 (see, e.g., FIGS. 4 and 6) that runs circumferentially around the exterior surface of the side of the nipple 132. The blade 108 also includes a notched surface 202 (see, e.g., FIGS. 2, 6 and 8). The notched surface 202 includes a plurality of notches that extend radially outward from the periphery of the nipple 132. The notched surface 202 is located toward the base of the nipple 132 on an upper surface 602 of the blade 108, and the notched surface 202 completely surrounds the nipple 132 (see, e.g., FIGS. 6 and 8).

The head 106 includes an opening 131 configured to receive the nipple 132. The head also includes a notched surface 204 (see, e.g., FIGS. 2, 6 and 7). The notched surface 204 includes a plurality of notches that extend radially outward from the periphery of the opening 131. The notched surface 204 is on a lower surface 702 of the head 106, and the notched surface 204 completely surrounds the opening 131 (see, e.g., FIG. 7). The notched surface 204 of the head 106 is configured to mate with the notched surface 202 of the blade 108, thereby securing the blade 108 relative to the head 106. The blade 108 can be swiveled radially about the head 106 three-hundred and sixty degrees and, because the blade's notched surface 202 completely surrounds the nipple 132 and the head's notched surface 204 completely surrounds the opening 131, the blade 108 can be secured in any position relative to the head 106 by mating the notched surfaces 202, 204.

The head 106 also includes a first corridor 502 (see, e.g., FIG. 5) in communication with a second corridor 503. The second corridor 503 runs substantially perpendicular to the first corridor 502 and is also in communication with the opening 131. Disposed in the first corridor 502 is a spring 504 attached to a plunger 506. The plunger 506 extends from the corridor 504 such that it can be manipulated by a user. The plunger 506 is generally cylindrical and includes a recess 508 that runs circumferentially around the exterior surface of the side of the plunger 506. Disposed in the second corridor 503 are ball bearings 510, 512. The ball bearings 510, 512 are held captive between the first corridor 502 and the opening 131. One end of the second corridor 503 includes a lip that is smaller in diameter than the ball bearing 512, such that the ball bearing 512 can extend from the second corridor 503 into the opening 131, but is still held captive by the second corridor 503. The other end of the second corridor 503 is in communication with the first corridor 502 such that the ball bearing 510 can contact the plunger 506.

Figure 5:
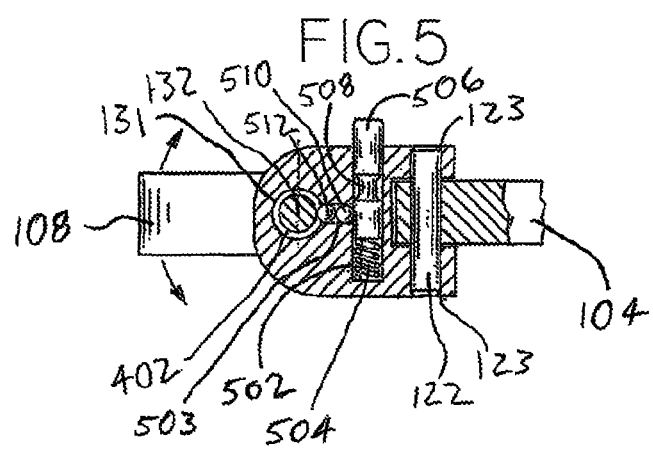
FIG. 5 depicts a top-sectional view of a portion of the surgical retractor in FIG. 4 taken about line 5-5.

In operation, when the plunger 506 is being depressed, the spring 504 is in a compressed state, and the recess 508 is aligned with the second corridor 503 such that the ball bearing 510 is allowed to extend from the second corridor 503 into the first corridor 502, thereby allowing the ball bearing 512 not to extend from the second corridor 503 into the opening 131. In this state, the nipple 132 on the blade 108 can be inserted into the opening 131, removed from the opening 131 and/or swiveled relative to the opening (thereby allowing the blade 108 to be swiveled radially about the head 106 as indicated in FIG. 5 by the arrows).

In operation, when the plunger 506 is not being depressed, the spring 504 is in an extended state, and an exterior surface of the plunger 506 (that is not the recess 508) is aligned with the second corridor 503 and exerts a force on the ball bearing 510, thereby forcing the ball bearing 512 to extend from the second corridor 503 into the opening 131. When the plunger 506 is not being depressed, the nipple 132 on the blade 108 cannot be received in the opening 131 of the head 106 because the ball bearing 512 is being forced to extend from the second corridor 503 into the opening 131, thereby blocking the opening 131. Also, when the plunger 506 is not depressed, a blade 108 that is already attached to the head 106 cannot be removed from the head 106 because the ball bearing 512 is being forced to extend from the second corridor 503 into the opening 131 and into the recess 402 on the nipple 132. Further, when the blade 108 is attached to the head 106 (and the ball bearing 512 is being forced to extend from the second corridor 503 into the opening 131 and into the recess 402 on the nipple 132) the notched surface 204 of the head 106 mates with the notched surface 202 of the blade 108, thereby securing the blade 108 relative to the head 106 such that the blade 108 cannot swivel radially about the head 106. This can provide for locking of the blade 108 in any radial position about the head 106.

In an alternative embodiment, the plunger/spring/ball bearing actuation system of the head 106 depicted and described in connection with FIGS. 1-8 can be replaced with an actuation system that includes a thumb screw. Such an embodiment is depicted, for example, in FIG. 9, which depicts a head 906 with a threaded opening 901 in communication with the opening 131 that is configured to receive the nipple 132 of the blade 108. In operation, a thumb screw 902 with external threads 903 configured to mate with the threaded opening 901 can be screwed into the threaded opening 901 until an end 904 of the screw 902 extends from the threaded opening 901 into the opening 131. When the screw 902 is unscrewed from the head 906 such that the end 904 of the screw 902 does not extend from the threaded opening 901 into the opening 131, the nipple 132 on the blade 108 can be inserted into the opening 131, removed from the opening 131 and/or swiveled relative to the opening (thereby allowing the blade 108 to be swiveled radially about the head 906). When the end 904 of the screw 902 extends from the threaded opening 901 into the opening 131, the nipple 132 on the blade 108 cannot be received in the opening 131 of the head 906 because the end 904 of the screw 902 is blocking the opening 131. Also, when a blade 108 is already attached to the head 906, the blade 108 cannot be removed from the head 906 because the end 904 of the screw 902 is extending from the threaded opening 901 into the opening 131 and into the recess 402 on the nipple 132. Further, when the blade 108 is attached to the head 906 (and the end 904 of the screw 902 is extending from the threaded opening 901 into the opening 131 and into the recess 402 on the nipple 132) a notched surface of the head 906 can mate with the notched surface 202 of the blade 108, thereby securing the blade 108 relative to the head 906 such that the blade 108 cannot swivel radially about the head 906. In certain embodiments, the thumb screw 902 can be screwed into the threaded opening 901 until the end 904 of the screw 902 contacts the nipple 132 of the blade 108, thereby securing the blade 108 in position relative to the head 906 such that the blade 108 cannot swivel radially about the head 906.

In an alternative embodiment, the threaded shaft/nut actuation system of the connector 104 depicted and described in connection with FIGS. 1-8 can be replaced with an actuation system that includes a notched shaft and a spring loaded lever. Such an embodiment is depicted, for example, in FIG. 10, which depicts a connector 1004 that includes a first end 1026 that is attachable to the arm 102. The connector also includes a second end 1028 (opposite the first end 1026) that is attachable to the head 106. The second end 1028 includes an opening configured to receive a pin 122. The head 106 includes a neck portion comprising opposing side walls, 118, 120. Each side wall 118, 120 of the head 106 is configured to receive the pin 122 in a circular opening 123. The connector 1004 also includes a notched shaft 1010 and a spring loaded lever 1012. One end of the shaft 1010 includes an opening configured to receive a pin 124. Each side wall 118, 120 of the head 106 is configured to receive the pin 124 in an opening 125. In operation, translation of the shaft 1010 can exert a force on pin 124, thereby causing rotation of the head 106 about pin 122. The side wall openings 125 in the head 106 are round on the ends and flat on the sides and allow the pin 124 to translate about the opening 125 during rotation of the head 106 about pin 122.

The notched shaft 1010 is retained by openings in a first wall 1014 and a second wall 1016 such that the notches can be contacted by the spring loaded lever 1012. The spring loaded lever 1012 is pivotally mounted on the first wall 1014 such that the spring loaded lever 1012 can pivot about pin 1050. When the spring loaded lever 1012 is not being actuated, the spring loaded lever 1012 contacts the notches in notched shaft 1010, thereby maintaining the notched shaft in its current position. When the spring loaded lever 1012 is actuated (by depressing an end of the lever 1012), the spring loaded lever 1012 releases the notches in the notched shaft 1010, thereby allowing the notched shaft to be translated in a first direction (direction a) or the opposite direction (direction b). Translation of the shaft 1010 in the direction a exerts a force on pin 124, thereby causing rotation of the head 106 about pin 122. This results in angular displacement of the blade 108 such that the distal end 130 of the blade 108 moves away from the arm 102. Translation of the shaft 1010 in the direction b exerts a force on pin 124, thereby causing rotation of the head 106 about pin 122. This results in angular displacement of the blade 108 such that the distal end 130 of the blade 108 moves toward the arm 102.

In an alternative embodiment, the arm 102, connector 104 and head 106 depicted and described in connection with FIGS. 1-8 can be replaced with an integrated structure that does not provide for angular displacement of the blade relative thereto. Such an embodiment is depicted, for example, in FIGS. 11-13 and 16, which depict an arm 1102 with an opening 1131 at one end. The opening 1131 is configured to receive a nipple 132 of a blade 108. The arm 1102 also includes a plunger 1156 in communication with a spring and a plurality of ball bearings similar to the plunger/spring/ball bearing actuation system described in connection with FIGS. 1-8. The arm also includes a notched surface 1204 (see, e.g., FIGS. 12-13). The notched surface 1204 includes a plurality of notches that extend radially outward from the periphery of the opening 1131. The notched surface 1204 is on a lower surface 1202 of the arm 1102, and the notched surface 1204 completely surrounds the opening 1131. The notched surface 1204 of the arm 1102 is configured to mate with the notched surface 202 of the blade 108, thereby securing the blade 108 relative to the arm 1102. The blade 108 can be swiveled radially about the arm 1102 three-hundred and sixty degrees and, because the blade's notched surface 202 completely surrounds the nipple 132 and the head's notched surface 1204 completely surrounds the opening 131, the blade 108 can be secured in any position relative to the arm 1102 by mating the notched surfaces 202, 1204.

In operation, when the plunger 1156 is being depressed, a ball bearing is not being forced to extend into the opening 1131, and the nipple 132 on the blade 108 can be inserted into the opening 1131, removed from the opening 1131 and/or swiveled relative to the opening (thereby allowing the blade 108 to be swiveled radially about arm 1102. When the plunger 1156 is not being depressed, a ball bearing is being forced to extend into the opening 1131, thereby blocking the opening such that the nipple 132 on the blade 108 cannot be received in the opening 1131 of the arm 1102. Also, when the plunger 1156 is not being depressed, a blade 108 that is already attached to the arm 1102 cannot be removed from the arm 1102 because the ball bearing is being forced to extend into the opening 1131 and into the recess 402 on the nipple 132. Further, when the blade 108 is attached to the arm 1102 (and the ball bearing is being forced to extend into the opening 131 and into the recess 402 on the nipple 132), the notched surface 1204 of the arm 1102 mates with the notched surface 202 of the blade 108, thereby securing the blade 108 relative to the arm 1102 such that the blade 108 cannot swivel radially about the arm 1102.

The arm 1102 (see, e.g., FIG. 16) is similar to the arm 102 (see, e.g., FIG. 1) in that the length of both arms are smooth and do not include any notches. Such arms are configured to be removably and movably attachable to a stationary device, such as a medical table, for example. Such arms can be translated relative to a stationary device by loosening any securing mechanism between the arm and the stationary device (such as a clasp, for example) and sliding the arm relative to the stationary device. The arm can then be re-secured to the stationary device when a desired position is obtained. In certain embodiments, the lack of notches and/or attachment to a smooth surface of an arm can provide more freedom to choose a desired position for the arm relative to the stationary device.

Figure 14:
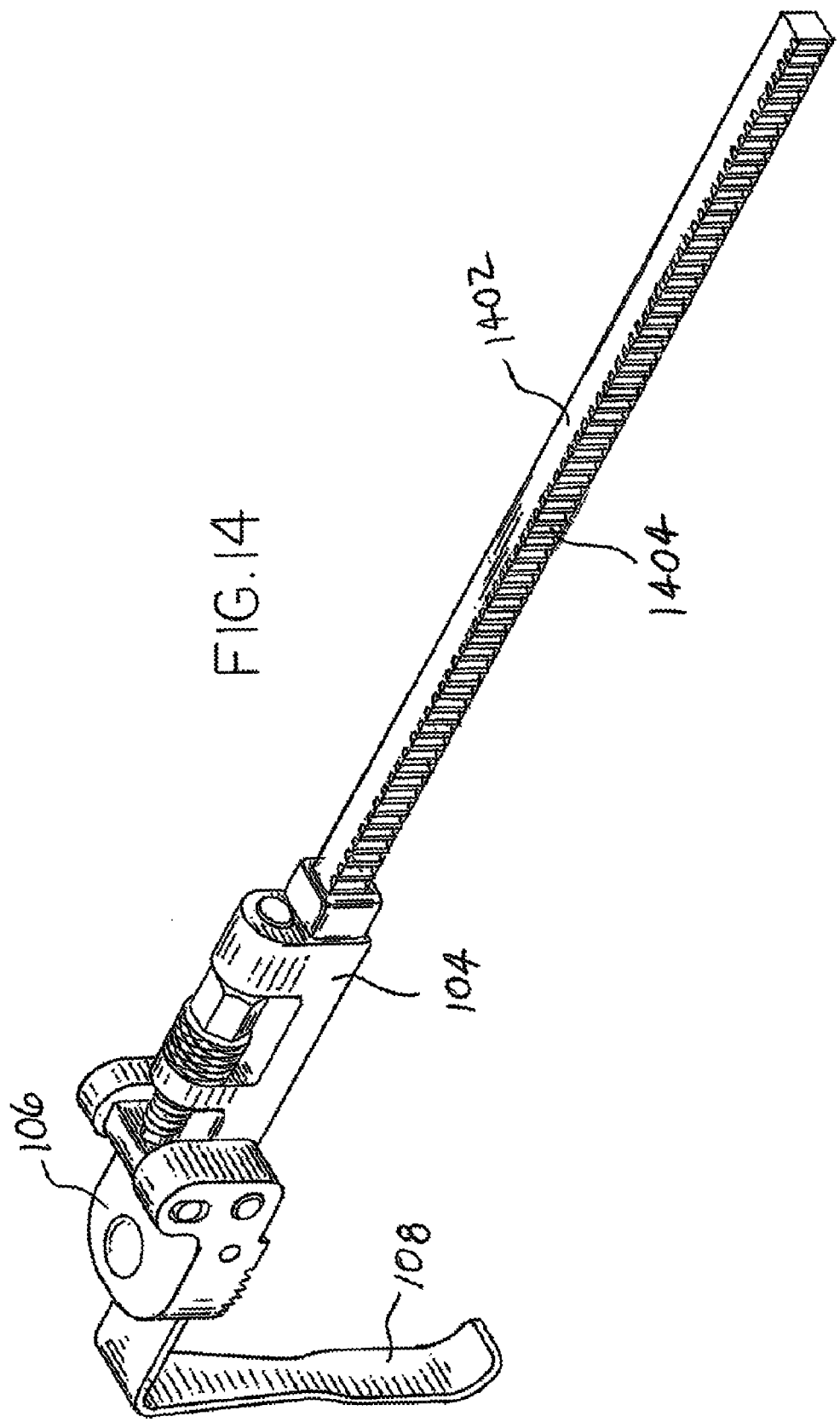
FIG. 14 depicts a perspective view of a surgical retractor used in accordance with an embodiment of the present technology.

In an alternative embodiment, the arm 102 (described in connection with FIGS. 1-8) or the arm 1102 (described in connection with FIGS. 11-13 and 16) can be replaced with a notched arm. Such embodiments are depicted, for example, in FIGS. 14 and 15, respectively. FIG. 14 depicts an arm 1402 with a notched surface 1404 in combination with a connector 104, head 106 and blade 108 (as described in connection with FIGS. 1-8). FIG. 15 depicts an arm 1502 with a notched surface 1504 in combination with an opening 1131 and plunger 1156 (as described in connection with FIGS. 11-13 and 16). The arms 1402, 1502 are configured to be removably and movably attachable to a stationary device, such as a medical table, for example. In certain embodiments, such arms 1402, 1502 can be translated relative to a stationary device using a cranking mechanism that mates with the notches 1404, 1504. In other embodiments, arms 1402, 1502 can be secured relative to a stationary device using a spring loaded lever that contacts the notches 1404, 1504 when the lever is not actuated. In such embodiments, the arm 1402, 1502 can be unsecured by actuating the lever and the arm 1402, 1502 can be translated by sliding the arm 1402, 1502 relative to the stationary device. The arm 1402, 1502 can then be re-secured to the stationary device when a desired position is obtained. In other embodiments, arms 1402, 1502 can be secured relative to a stationary device using a latch that contacts the notches 1404, 1504 when the latch is in a closed position. In such embodiments, the arm 1402, 1502 can be unsecured by moving the latch to an open position, and the arm 1402, 1502 can be translated by sliding the arm 1402, 1502 relative to the stationary device. The arm 1402, 1502 can then be re-secured to the stationary device when a desired position is obtained. In certain embodiments, using notches on an arm can provide for improved secure attachment to a stationary device.

Figure 17:
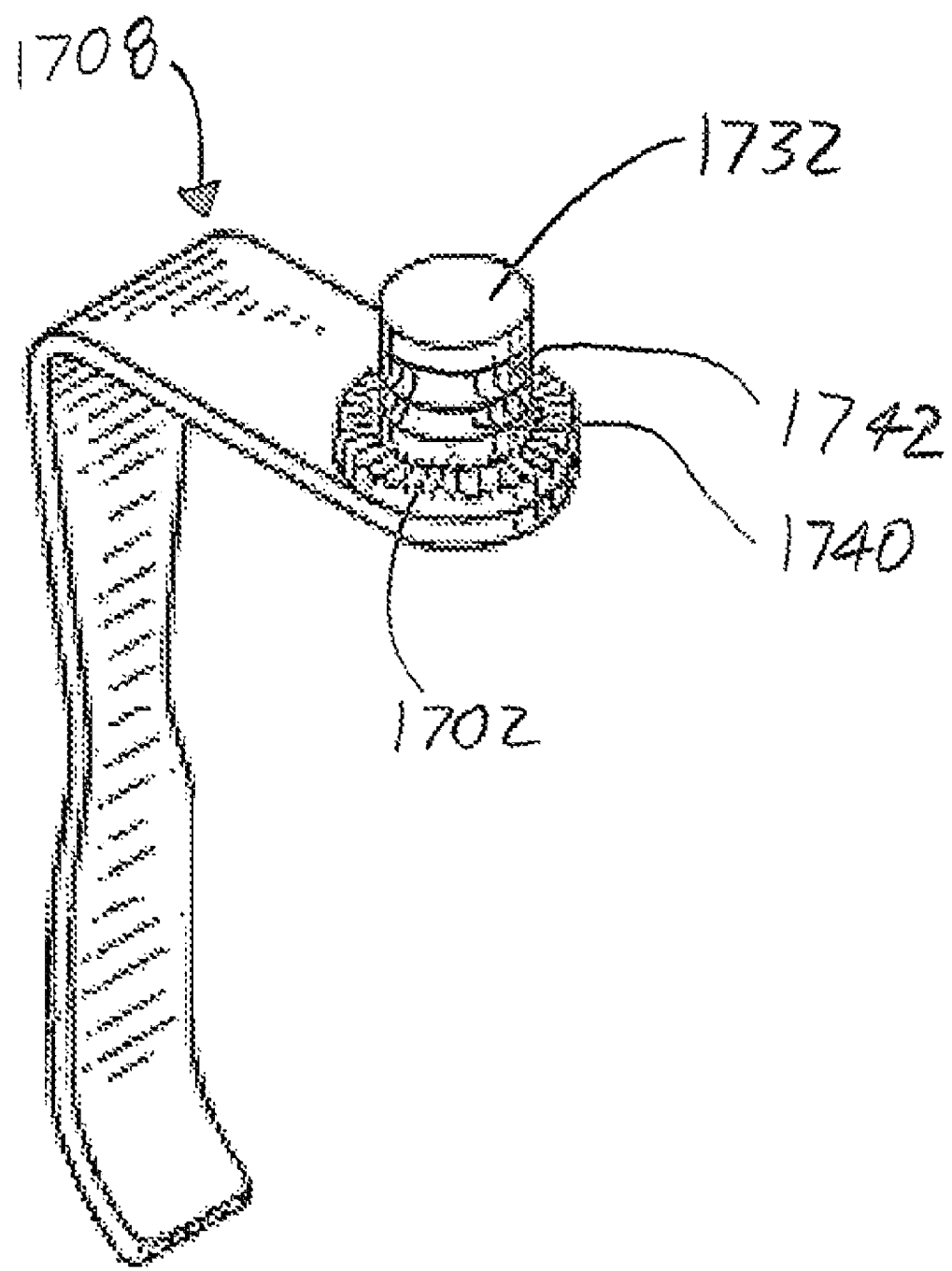
FIG. 17 depicts a perspective view of a portion of a surgical retractor used in accordance with an embodiment of the present technology.

In an alternative embodiment, a blade can be configured like the blade 108 shown and described in connection with FIGS. 1-8 and can also include a second recess in the nipple. The second recess can be configured so as to allow the blade to be attached to the head such that the notched surface of the blade and the notched surface of the head do not mate, thereby allowing the blade to swivel freely about the head. Such an embodiment is depicted, for example, in FIG. 17, which depicts a blade 1708 comprising a notched surface 1702 and a nipple 1732 that includes a first recess 1740 and a second recess 1742. The first recess 1740 is located in closer proximity to the notched surface 1702 than the second recess 1742. When the blade 1708 is attached to the head 106, it can be attached to the first recess 1740 such that the ball bearing 512 is extending into the opening 131 and into the first recess 1740 on the nipple 1732, and such that the notched surface 204 of the head 106 mates with the notched surface 1702 of the blade 1708, thereby securing the blade 1708 relative to the head 106 such that the blade 1708 cannot swivel radially about the head 106. This can provide for locking of the blade 108 in any radial position about the head 106. Also, when the blade 1708 is attached to the head 106, it can be attached to the second recess 1742 such that the ball bearing 512 is extending into the opening 131 and into the second recess 1742 on the nipple 1732, and such that the notched surface 204 of the head 106 does not mate with the notched surface 1702 of the blade 1708, thereby allowing the blade 1708 to swivel freely about the head 106.

Figure 18:
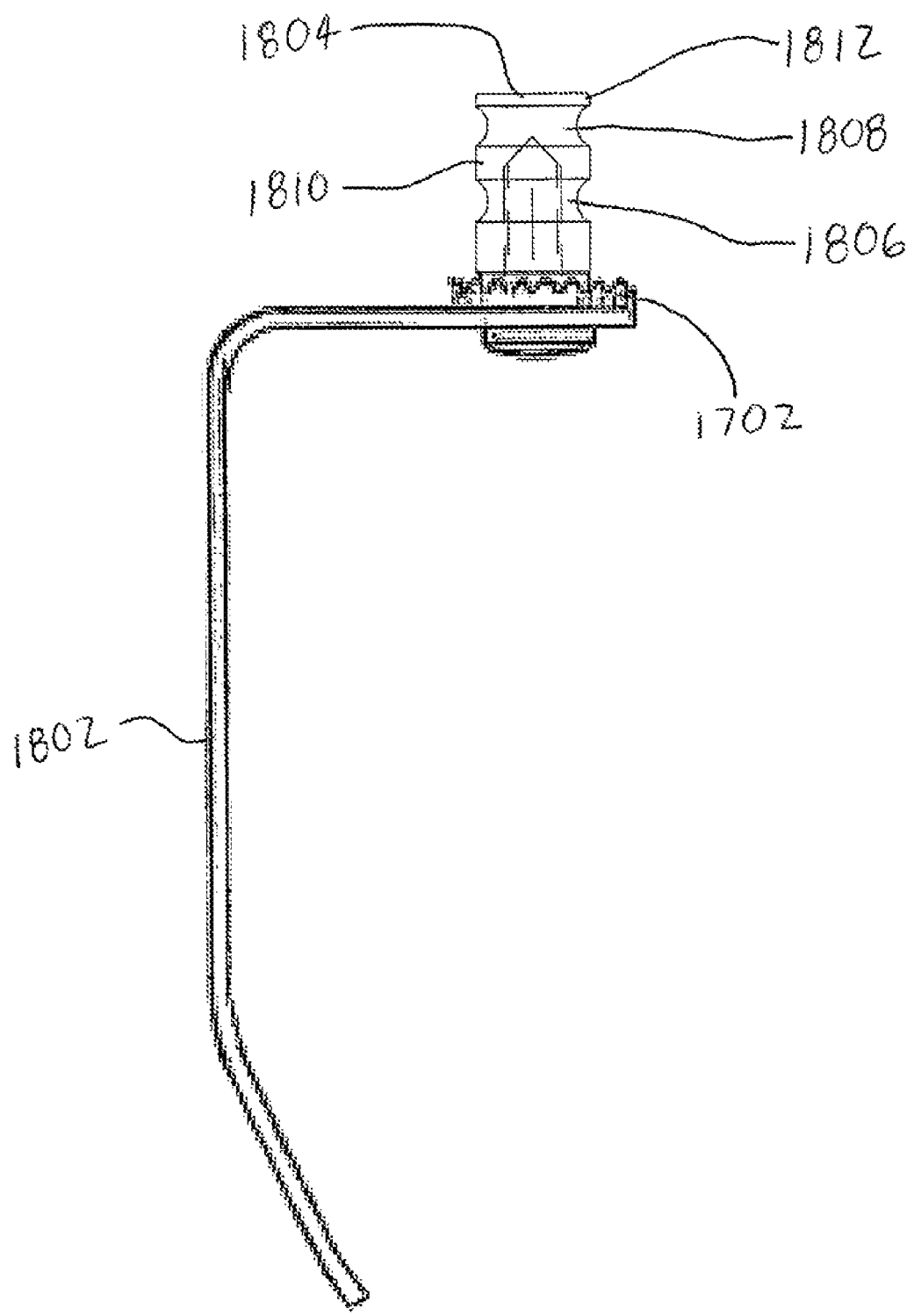
FIG. 18 depicts a side view of a portion of a surgical retractor used in accordance with an embodiment of the present technology.
Figure 19:
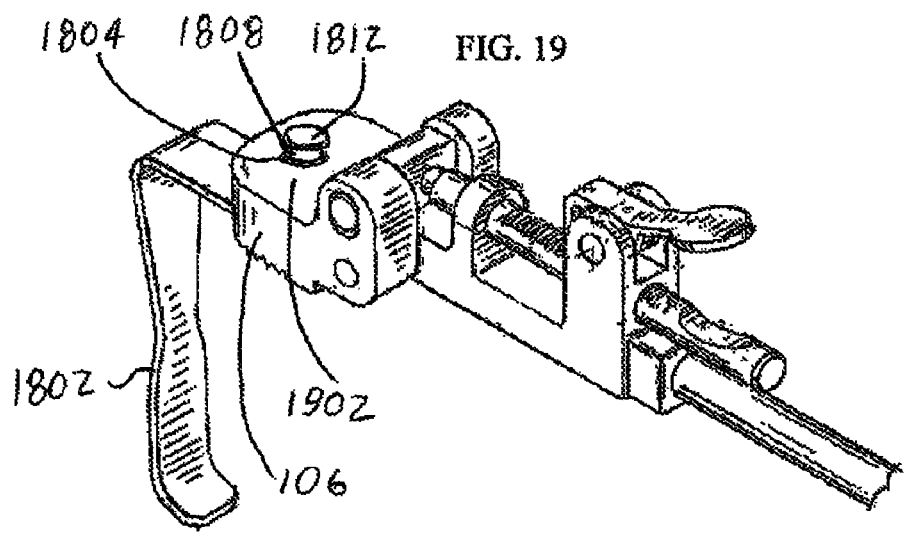
FIG. 19 depicts a perspective view of a portion of a surgical retractor used in accordance with an embodiment of the present technology.

FIGS. 18-19 depict an alternative embodiment, where blade 1802 includes an elongated nipple 1804 that includes a first peripheral recess 1806 configured to receive ball bearing 512 and a second peripheral recess 1808. As depicted in FIG. 18, first peripheral recess 1806 and second peripheral recess 1808 are vertically separated by a portion 1810 of nipple 1804, and second peripheral recess 1808 terminates at peripheral flange 1812. As depicted in FIG. 19, second peripheral recess 1808 and peripheral flange 1812 can extend beyond an upper surface 1902 of head 106 when blade 1802 is attached thereto.

Figure 20:
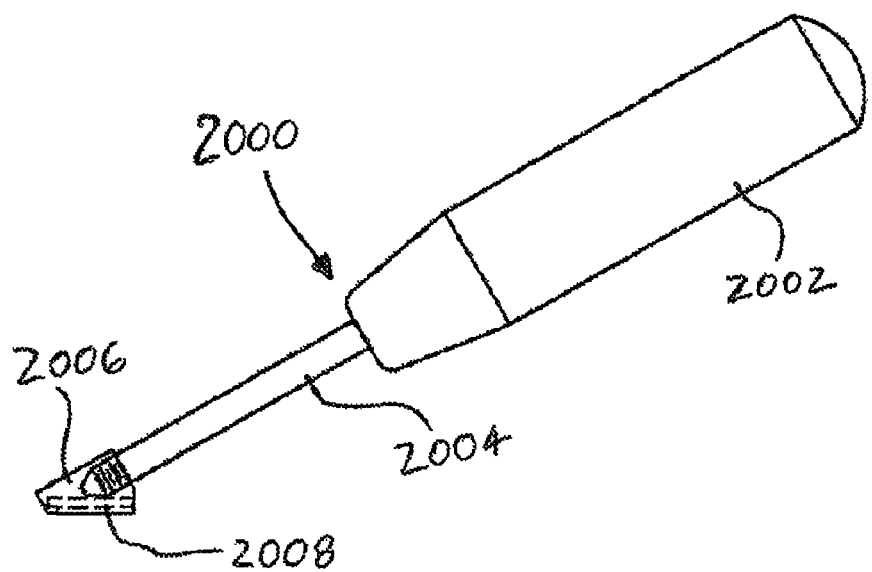
FIG. 20 depicts a side view of a surgical retractor blade angling device used in accordance with an embodiment of the present technology.
Figure 21:
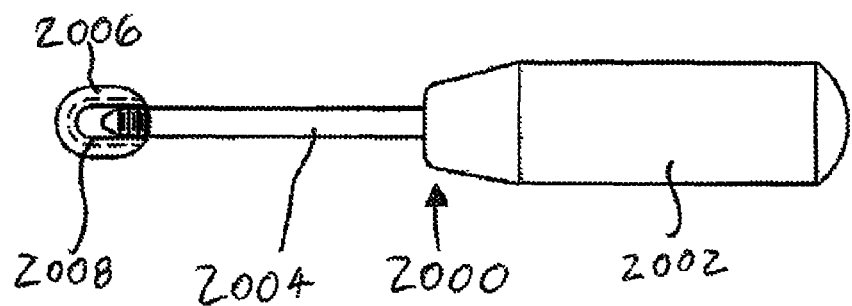
FIG. 21 depicts a bottom view of the surgical retractor blade angling device depicted in FIG. 20.
Figure 22:
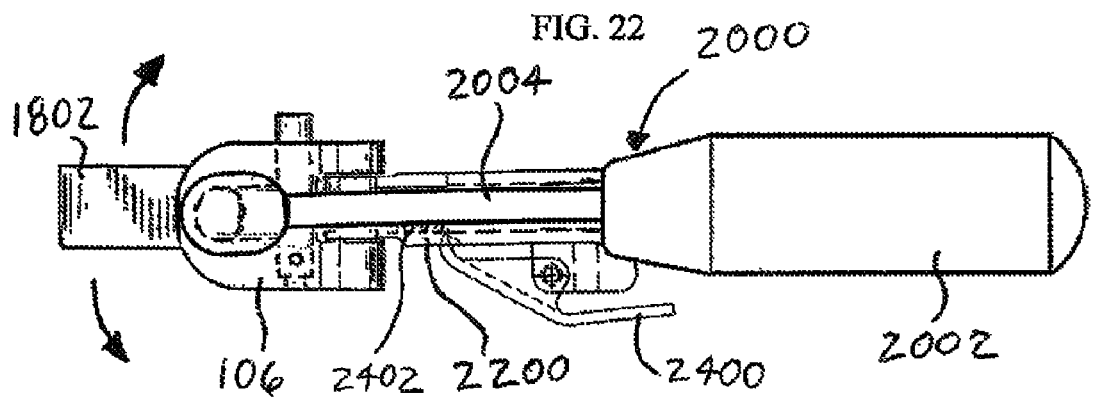
FIG. 22 is a top view of a surgical retractor with the surgical retractor blade angling device depicted in FIG. 20 attached thereto.
Figure 23:
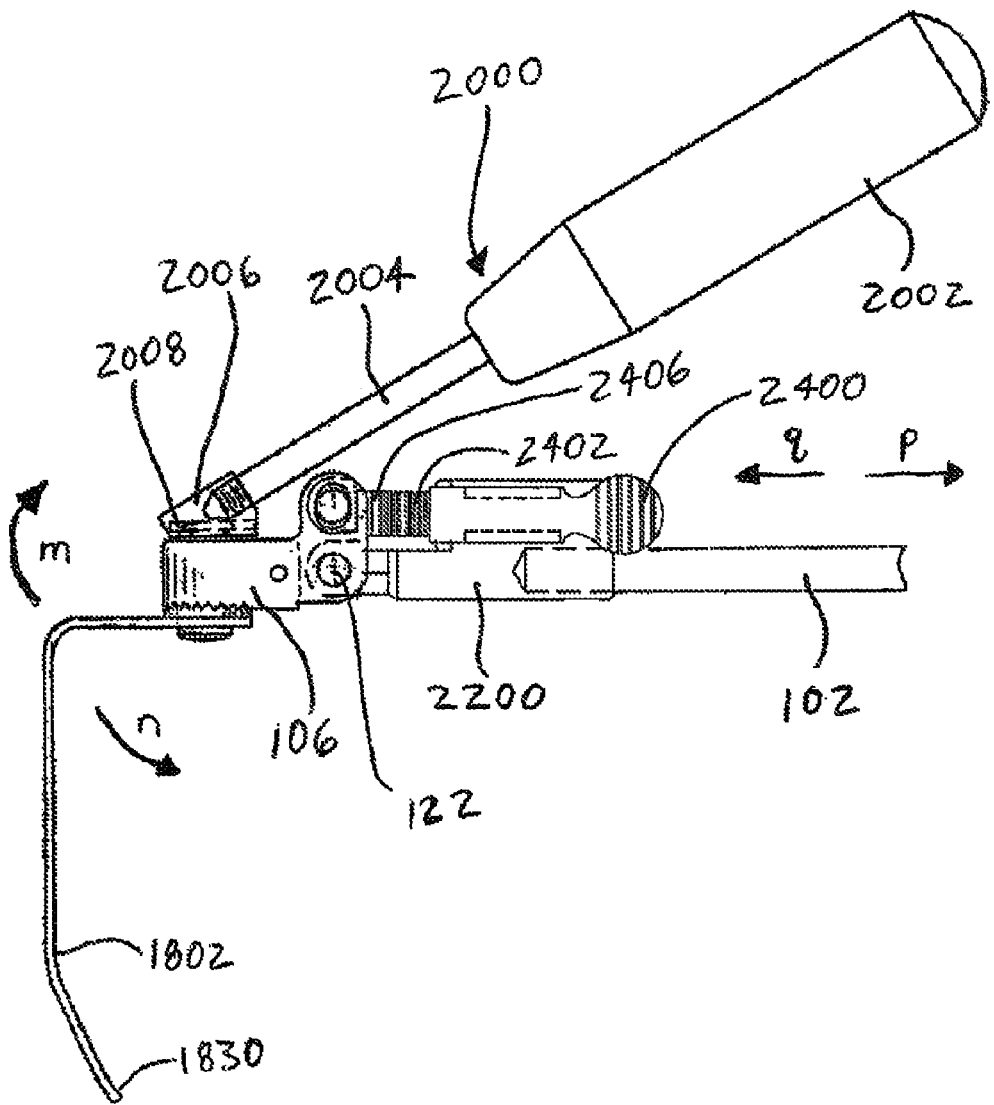
FIG. 23 is a side view of a surgical retractor with the surgical retractor blade angling device depicted in FIG. 20 attached thereto.

FIGS. 20-21 depict a surgical retractor blade angling device 2000 used in accordance with an embodiment of the present technology. FIGS. 22-23 depict a surgical retractor with the surgical retractor blade angling device 2000 attached thereto. The surgical retractor depicted in FIGS. 22-23 includes blade 1802, head 106, connector 2200 and arm 102. Surgical retractor blade angling device 2000 includes handle 2002, arm 2004 and head 2006. Head 2006 includes slot 2008 configured to receive peripheral flange 1812.

In operation, slot 2008 can be aligned with peripheral flange 1812 and slid onto flange 1812 in order to attach angling device 2000 to the surgical retractor. When attached, arm 2004 and handle 2002 of surgical retractor blade angling device 2000 can extend from head 106 of surgical retractor at an angle, as depicted in FIG. 23.

Angling device 2000 can be used to swivel blade 1802 radially about head 106, as indicated in FIG. 22, by manipulating handle 2002. As indicated in FIG. 23, angling device 2000 can also be used to rotate head 106 about pin 122 by manipulating handle 2002, thereby providing angular displacement of blade 1802 such that distal end 1830 of blade 1802 moves toward or away from surgical retractor arm 102. Once a desired blade position is achieved, angling device 2000 can be removed from the surgical retractor by sliding slot 2008 off of peripheral flange 1812.

Slot 2008 can be configured to provide a tension fit with flange 1812. In certain embodiments, slot 2008 can be configured with a varied clearance that decreases deeper into slot 2008, such that sliding flange 1812 deeper into slot 2008 can increase the tension between the two. Flange 1812 is circular, but can be otherwise configured in other embodiments, such as rectangular or triangular, for example.

Connector 2200 includes a trigger locking mechanism similar to the mechanism shown and described in connection with FIG. 10. Connector 2200 is depicted in FIGS. 22-23 and includes a trigger 2400 in operable relation with notched shaft 2406 including teeth 2402. Connector 2200 differs from connector 1004 depicted in FIG. 10 in that trigger 2400 and teeth 2402 are configured as a ratchet mechanism. That is, while engagement of trigger 2400 and teeth 2402 restricts movement of shaft 2406 in the direction p (shown in FIG. 23), engagement of trigger 2400 and teeth 2402 does not restrict movement of shaft 2406 in the direction q (shown in FIG. 23). This configuration can restrict rotation of head 106 about pin 122 in the direction m (shown in FIG. 23) unless trigger 2400 is actuated (such that trigger 2400 does not engage teeth 2402). This configuration can also allow unrestricted rotation of head 106 about pin 122 in the direction n (shown in FIG. 23), even if trigger 2400 is not actuated. In operation, such a ratchet mechanism can allow angular displacement of blade 1802 in the direction n (shown in FIG. 23) without requiring a user to actuate trigger 2400.

Certain embodiments may include some or all of the features described herein in any workable combination. Certain embodiments may implement the elements described herein as separate components or as integrated components.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A surgical retractor system comprising:
   a head with an opening, wherein the head is linearly movable along a support in a direction along a first axis and rotatable about a second axis that is generally perpendicular to the first axis;
   a blade comprising a nipple including a recess that runs circumferentially around an exterior surface of the nipple and terminates at a flange, wherein the opening is configured to receive the nipple, and wherein the nipple is longer than the opening such that the flange extends beyond an end of the opening when the blade is attached to the head;
   an actuator configured to move the head linearly along the first axis, wherein the linear movement causes rotational movement of the head about the second axis;
   an angling device comprising a handle, the angling device configured to receive the nipple;
   a first securement engaging the nipple to releasably secure the blade to the angling device; and a second securement disposed between the head and the blade, wherein the second securement allows releasable rotation of the blade with respect to the head about a third axis that is generally perpendicular to both the first axis and the second axis, wherein rotation of the blade about the third axis is facilitated through rotation of the angling device.

2. The system of claim 1, wherein the angling device is co-rotatable with the blade about the opening when the angling device is attached to the nipple.

3. The system of claim 1, wherein the actuator comprises a notched shaft and a spring loaded lever, wherein manipulating the spring loaded lever can release the notched shaft such that the shaft can be translated along the first axis.

4. The system of claim 3, wherein the notched shaft and the spring loaded lever are configured to work as a ratchet, such that when the shaft and the lever are engaged, translation of the shaft along the first axis in a first direction is restricted and translation of the shaft along the first axis in a second direction opposite the first direction is not restricted.

5. The system of claim 1, wherein the flange is circular.

6. The system of claim 1, wherein the angling device is configured to extend from the head at an angle.

7. The system of claim 1, wherein the angling device includes a slot configured to receive the flange.

8. The system of claim 7, wherein the slot is configured to have a varied clearance that decreases deeper into the slot, such that sliding the flange deeper into the slot can increase tension between the flange and the slot.

9. The system of claim 1, wherein the actuator comprises a threaded shaft and corresponding nut assembly.

10. The system of claim 1, wherein the first securement comprises:
- an arm extending from the handle of the angling device and terminating at connection threads; and
- an angling device head having a first opening configured to accept the nipple, wherein the angling device head further comprises a second opening having connection threads configured for connection with the connection threads of the arm extending from the handle of the angling device, wherein rotation of the arm in a first direction directs the arm into engagement with the flange of the nipple, and wherein rotation of the arm in a second direction removes the arm from engagement with the flange of the nipple.

11. The system of claim 1, wherein the second securement comprises notched surfaces disposed between the blade and the head.

* * * * *